(12) United States Patent
Pamula et al.

(10) Patent No.: US 8,317,990 B2
(45) Date of Patent: Nov. 27, 2012

(54) DROPLET ACTUATOR LOADING AND TARGET CONCENTRATION

(75) Inventors: Vamsee K. Pamula, Durham, NC (US); Michael G. Pollack, Durham, NC (US); Vijay Srinivasan, Durham, NC (US)

(73) Assignee: Advanced Liquid Logic Inc., Research Triangle Park, NC (US)

( * ) Notice: Subject to any disclaimer, the term of this patent is extended or adjusted under 35 U.S.C. 154(b) by 431 days.

(21) Appl. No.: 12/531,835

(22) PCT Filed: Mar. 24, 2008

(86) PCT No.: PCT/US2008/057963
§ 371 (c)(1),
(2), (4) Date: Oct. 15, 2009

(87) PCT Pub. No.: WO2008/118831
PCT Pub. Date: Oct. 2, 2008

(65) Prior Publication Data
US 2010/0062508 A1 Mar. 11, 2010

Related U.S. Application Data

(60) Provisional application No. 60/896,643, filed on Mar. 23, 2007, provisional application No. 60/980,529, filed on Oct. 17, 2007, provisional application No. 61/017,880, filed on Dec. 31, 2007.

(51) Int. Cl.
*G01N 35/08* (2006.01)
*G01N 33/543* (2006.01)
(52) U.S. Cl. .................................. 204/450; 204/600
(58) Field of Classification Search .......... 204/450, 204/600
See application file for complete search history.

(56) References Cited

U.S. PATENT DOCUMENTS
3,665,678 A * 5/1972 Kammermeyer et al. ...... 95/174
(Continued)

FOREIGN PATENT DOCUMENTS
WO WO 2006/102516 A2 9/2006
(Continued)

OTHER PUBLICATIONS

Jie Ding, "System level architectural optimization of semi-reconfigurable microfluidic system," M.S. Thesis, Duke University Dept of Electrical Engineering, 2000.

(Continued)

*Primary Examiner* — Kaj K Olsen
(74) *Attorney, Agent, or Firm* — Ward & Smith P.A.; William A. Barrett

(57) ABSTRACT

A droplet actuator and method of providing a droplet comprising an target substance on the droplet actuator, and including discrete flow and continuous flow functionality. Discrete flow function is controlled by electrodes arranged for conducting droplet operations on a substrate surface. The continuous flow function includes a fluid path arranged for flowing a fluid therethrough. The discrete flow and continuous flow functions may be by a barrier, including a second fluid path through the barrier. The continuous flow function may include a capture surface comprising a component having an affinity for the target substance. Methods of the invention may include flowing a fluid comprising the target substance through the fluid path; capturing the target substance on the capture surface; and forming a droplet in the discrete flow region via the second fluid path and the electrodes comprising the captured target substance.

37 Claims, 7 Drawing Sheets

U.S. PATENT DOCUMENTS

| | | | |
|---|---|---|---|
| 5,993,627 A * | 11/1999 | Anderson et al. | 204/456 |
| 6,294,063 B1 | 9/2001 | Becker et al. | |
| 6,524,456 B1 | 2/2003 | Ramsey et al. | |
| 6,558,944 B1 | 5/2003 | Parce et al. | |
| 2003/0082081 A1 * | 5/2003 | Fouillet et al. | 422/105 |
| 2004/0058450 A1 | 3/2004 | Pamula et al. | |
| 2006/0108012 A1 * | 5/2006 | Barrow et al. | 137/806 |
| 2006/0186048 A1 * | 8/2006 | Tan | 210/656 |
| 2006/0254933 A1 | 11/2006 | Adachi et al. | |

FOREIGN PATENT DOCUMENTS

| | | |
|---|---|---|
| WO | WO 2006/138543 A1 | 12/2006 |

OTHER PUBLICATIONS

Moon, Hyejin, Ph.D., "Electrowetting-on-dielectric microfluidics: Modeling, physics, and MALDI application," University of California, Los Angeles, 2005.

Pollack et al., "Electrowetting-Based Actuation of Droplets for Integrated Microfluidics," Lab on a Chip (LOC), vol. 2, pp. 96-101, 2002.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

* cited by examiner

DROPLET ACTUATOR LOADING AND TARGET CONCENTRATION

1 RELATED PATENT APPLICATIONS

This application claims priority to U.S. Patent Application No. 60/896,643, filed on Mar. 23, 2007, entitled "Pre-concentration of an analyte"; U.S. Patent Application No. 60/980,529, filed on Oct. 17, 2007, entitled "Pre-concentration of an analyte"; and U.S. Patent Application No. 61/017,880, filed on Dec. 3, 2007, entitled "Droplet actuator loading and target concentration"; the entire disclosures of which are incorporated herein by reference.

2 GOVERNMENT INTEREST

This invention was made with government support under DK066956-02 and GM072155-02 awarded by the National Institutes of Health of the United States. The United States Government has certain rights in the invention.

3 BACKGROUND

Droplet actuators are used to conduct a wide variety of droplet operations. A droplet actuator typically includes a substrate associated with droplet operation electrodes, which are arranged in a manner which permits certain droplet operations to be performed on a surface of the substrate. In some cases, the droplet actuator also includes a top plate separated from the surface of the substrate in a manner which creates a gap in which the droplet operations may be performed. Typically the droplets are at least partially surrounded by filler fluid that is immiscible with the droplets. The surface of the substrate and other surfaces exposed to the filler fluid and/or the droplet are typically made from or coated with a material which is hydrophobic relative to the droplets being manipulated.

Referring to the applicants unpublished patent applications, which are cited herein, certain kinds of droplets may be subjected to various droplet operations on a droplet actuator to conduct certain kinds of droplet-based protocols. Where the droplet-based protocols involve detection of an analyte that is present in an initial sample in scarce amounts, there is a need for approaches to concentrating the analyte for analysis in the very small droplets that are used on the droplet actuator.

4 BRIEF DESCRIPTION OF THE INVENTION

In addition to the methods described herein, the invention provides new droplet actuators. For example, in one embodiment, the invention provides a droplet actuator with a substrate divided into a discrete flow section and a continuous flow section. In another embodiment, the invention provides a droplet actuator with a discrete flow substrate and a continuous flow substrate fluidly coupled by a fluid flow path. The discrete flow section may include electrodes arranged for conducting droplet operations on a substrate surface. The continuous flow section may include a fluid path arranged for flowing a fluid therethrough. The discrete flow and continuous flow sections may be separated by a barrier. The barrier may include an opening arranged relative to the electrodes such that fluid in the fluid path is in proximity to one or more of the electrodes. The continuous flow section may include a capture surface comprising a component having an affinity for the target substance.

The invention also provides a method of providing a droplet comprising an target substance on a droplet actuator. In operation, a method of the invention may proceed as follows: flowing a fluid comprising the target substance through the fluid path; capturing the target substance on the capture surface; forming a droplet comprising the captured target substance in the discrete flow section. The method may also include transporting the target substance through the opening and into the discrete flow section. A droplet may be formed in the discrete flow section by conducting droplet operations using the electrodes to draw fluid comprising the sample of interest through the opening and forming a droplet therefrom.

In some cases, the droplet actuator further includes sample collection beads immobilized in the fluid path such that a target substance in a fluid flowing through the fluid path is collected on the beads. Forming a droplet in the discrete flow section may involve transporting a droplet comprising the beads through the opening and into the droplet actuation region.

The droplet including the captured target substance in the discrete flow section is in certain embodiments at least partially surrounded by a filler fluid. The droplet including the captured target substance in the discrete flow section is in certain other embodiments substantially completely surrounded by a filler fluid. The droplet including the captured target substance in the discrete flow section may include one or more beads and/or one or more biological cells.

In some embodiments, the continuous flow section includes a second set of electrodes. These electrodes may, for example, be arranged for conducting droplet operations. Such an arrangement facilitates forming one or more sample droplets on the second set of electrodes, and transporting said one or more sample droplets into the discrete flow section. In another embodiment, such an arrangement facilitates forming one or more sample droplets on the second set of electrodes, and using the second set of electrodes to transport said one or more sample droplets into proximity with electrodes in the discrete flow section.

In some cases, the continuous flow section includes two or more capture surfaces. For example, the two or more capture surfaces may each comprise a different population of beads, and each population may have affinity for a different target substance.

In some embodiments employing beads, the beads are maintained in place by one or more physical barriers and/or one or more magnetic fields (e.g., a magnetic field produced by an electromagnet and/or by a permanent magnet).

Capturing the target substance on the capture surface may in some cases may involve combining one or more beads having affinity for the target substance with a fluid comprising the target substance prior to introduction of the fluid into the fluid path. The target substance may, for example, include an analyte of interest and/or a product of a chemical reaction. The target substance may in other cases include a bead and/or a biological cell. The target substance may include a bead comprising a analyte of interest and/or a product of a chemical reaction.

In some cases, the discrete flow section is fluidly coupled to the continuous flow section by a fluid path including a reservoir and a reservoir electrode associated with a surface thereof. Such embodiments may facilitate a method involving flowing a fluid comprising the substance of interest from the fluid path into the reservoir; and dispensing droplets from the reservoir onto one or more electrodes in the discrete flow section.

Flowing a fluid comprising the target substance through the fluid path may in some cases involve forcing fluid through the fluid path using a pressure source. The pressure source may, for example, be a pump or a syringe coupled to the fluid path.

Forming a droplet comprising the captured target substance in the discrete flow section may, in one embodiment, involve activating one of more electrodes in the discrete flow section adjacent to the opening to cause fluid to flow from the fluid path into the discrete flow section and form the droplet. In another embodiment, forming a droplet comprising the captured target substance in the discrete flow section may involve forcing fluid from the fluid path through the opening into the discrete flow section into proximity with one or more electrodes, and conducting droplet operations using the one of more electrodes to form the droplet. The force applied may cause a pressure in the fluid path which forces fluid through the opening into the discrete flow section into proximity with the one or more electrodes.

In one embodiment, the method of the invention conducts a chemical or biochemical reaction or interaction. Such a method may comprise providing a droplet actuator of the invention; flowing a fluid comprising the target substance through the fluid path; capturing the target substance on the capture surface; and conducting one or more droplet operations using the electrodes to transport a reagent into contact with the target substance and thereby conduct a chemical or biochemical reaction or interaction. In certain embodiments, the target substance comprises a cell and the biochemical interaction comprises interaction of the reagent with the cell.

In another aspect of the invention the method involves flowing a filler fluid comprising the droplet through the fluid path; and causing the droplet to pass through the opening into proximity with one or more of the electrodes to permit one or more electrode mediated droplet operations to be performed on the droplet.

Various embodiments may involve recirculating the filler fluid through the fluid path via a recirculation path. The recirculation path may in some embodiments comprises a filler fluid reservoir. Recirculation may be facilitated using a pump to cause filler fluid to flow through the recirculation path.

Droplet formation may be mediated by one or more of the electrodes described above, and may in some cases be assisted by a pressure forcing the droplet through the opening in the barrier.

Various other embodiments of the invention will be apparent from the description of the invention set forth in the ensuing sections.

5 DEFINITIONS

As used herein, the following terms have the meanings indicated.

"Activate" with reference to one or more electrodes means effecting a change in the electrical state of the one or more electrodes which results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator; configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads.

"Droplet" means a volume of liquid on a droplet actuator which is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a spiltting operation on a droplet, yielding one droplet with substantially all of the beads and one droplet substantially lacking in the beads.

"Magnetically responsive" means responsive to a magnetic field. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

The terms "top" and "bottom" are used throughout the description with reference to the top and bottom substrates of the droplet actuator for convenience only, since the droplet actuator is functional regardless of its position in space.

When a given component such as a layer, region or substrate is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct droplet operations on the droplet, the droplet is arranged on the droplet actuator in a manner which facilitates sensing of a property of or a signal from the droplet, and/or the droplet has been subjected to a droplet operation on the droplet actuator.

6 BRIEF DESCRIPTION OF THE DRAWINGS

7 DESCRIPTION

The invention provides a droplet actuator configured for processing input fluids to concentrate one or more target substances (e.g., analytes, products and/or beads containing analytes or products) and provide droplets including the concentrated target substances. For example, the target substances may be analytes or substances associated with one or more analytes (e.g., antibodies bound to analytes), and the droplets may be used in droplet-based protocols for analyzing the analytes. The invention also provides methods of making and using such droplet actuators. In general, the methods relate to preparing small volume sample droplets from large volume samples. In certain embodiments, the concentration of one or more target substances in the resulting small volume sample droplets is greater than the concentration of one or more target substances in the starting sample fluid.

The invention also relates to methods of loading reagents or any kinds of droplets onto a droplet actuator. For example, a filler fluid may be flowed through a continuous flow section of a droplet actuator (as described herein), droplets may be introduced into the continuous flow section and when the droplets are flowed into proximity with a discrete flow section, the droplets may be transported onto the discrete flow section and subjected to droplet operations. In this arrangement, the filler fluid may circulate back to a filler fluid reservoir.

The small volume fluid droplets containing the target substance may be subjected to one or more droplet operations on the droplet actuator. The droplet operations may be part of a droplet-based assay protocol to analyze the droplets for the target substance. In order to analyze larger volumes of starting fluid, multiple unit sized droplets may be analyzed in parallel and/or in sequence. Such an approach is suitable, for example, when the target substance is present at a very low concentration. Prior to introduction of a fluid into the droplet actuator of the invention, various concentration methods may be employed to pre-concentrate the target substance. Examples include centrifugation and/or filtration.

7.1 Fluid Processing Designs

Figure 1:
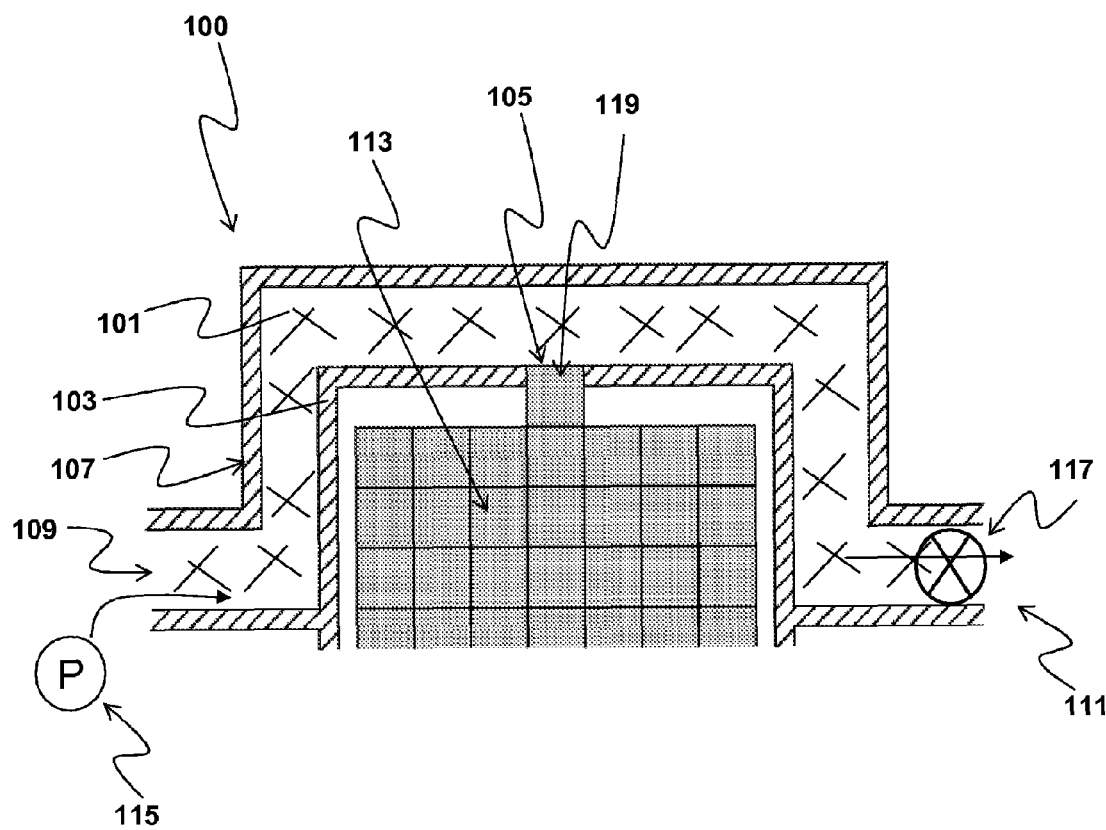
FIG. 1 illustrates a droplet actuator having target substance concentrating capabilities, and divided into a continuous flow section and a discrete flow section.

FIG. 1 illustrates a droplet actuator 100 having target substance concentrating capabilities. Droplet actuator 100 is divided into a continuous flow section and a discrete flow section.

The continuous flow section is represented by fluid path 101 through which fluid containing a target substance may be flowed. Fluid path 101 is defined by barriers 103 and 107. Barrier 103 separates the continuous flow section from the discrete flow section of droplet actuator 100. One or more openings in barrier 103, shown in the example as opening 119, may provide a fluid passage from the continuous flow section to the discrete flow section of the device.

The discrete flow section is represented by the array 113 of electrodes, which may be any arrangement of electrodes suitably configured to conduct droplet operations on droplets formed from fluid flowing through fluid path 101. In operation, a fluid may be flowed through inlet 109, through fluid path 101, and out through outlet 111, optionally via valve 117. One or more electrodes, represented in the example as electrode 105, may be provided in proximity to opening 119 to facilitate droplet operations using fluid from the continuous flow section. For example, such electrodes may be used to facilitate flow of fluid from the continuous flow section into the discrete flow section of droplet actuator 100 and/or formation of droplets from flow of droplets from such fluid. In one embodiment, fluid is circulated through fluid path 101.

As an example, a fluid containing an analyte of interest may be flowed through fluid path 101. As the fluid passes opening 119, electrode 105 may be activated, causing fluid from fluid path 101 to flow onto electrode 105. Additional electrodes from the array 113 of electrodes may be activated/deactivated in various patterns to form a droplet from the fluid on electrode 105 and conduct various droplet operations using the droplet. Flow of fluid onto electrode 105 may also be facilitated by restricting outflow of fluid path 101, relative to inflow, e.g., by constricting or closing valve 117 while pressure source 115 continues to force fluid into fluid path 101.

As another example, the fluid flowed through path 101 may be a filler fluid including one or more droplets, such as reagent droplets. The transport of reagent droplets from the continuous flow channel 101 onto the discrete flow section may, for example, be mediated by electrode 105 and adjacent electrodes. Impedance sensing may be used to determine when a droplet flowing through path 101 is in sufficient proximity to electrode 105 to be subjected to droplet operations mediated by electrode 105. In another embodiment, droplets in filler fluid in fluid path 101 may be forced into the discrete flow section by closing valve 117 causing flow of fluid through path 101 to divert through opening 119 into the discrete flow portion. Similarly, a suction may be applied to filler fluid in the discrete flow portion to force a droplet from path 101 through opening 105 and into the discrete flow section.

Filler fluid exiting fluid path 101, e.g., via outlet 111, may be flowed into a waste reservoir or recirculated to inlet 109 via a fluid path (not shown), optionally including filler fluid reservoir. Outside the droplet actuator, the droplet may be introduced into a filler fluid line that flows into path 101 using a variety of approaches. For example, the droplet may be injected into the filler fluid line. Similarly, the droplet may be deposited in a filler fluid reservoir having an outflow at a lower portion. The droplet may be permitted to sink (due to relative density of the filler fluid) to the bottom of the reservoir where it will flow into the filler fluid line and into fluid path 101.

Various approaches may be used to concentrate the target substance in fluid path 101 prior to introduction of fluid from fluid path 101 into the discrete flow section of droplet actuator 100. Such approaches serve to provide a droplet on the droplet actuator in which the target substance is more concentrated than in a starting fluid. The means of concentrating the target substance may, for example, involve capture of the target substance by a binder. The binder may be attached to a surface. The surface may be, for example, a surface of a bead, such as a magnetically responsive bead or a non-magnetically responsive bead. The surface may also alternatively be a fixed surface, such as an inner surface of the droplet actuator.

In one embodiment, the fluid containing the target substance is flowed through fluid path 101, where it is exposed to the capture surface. The capture surface may be a surface that is arranged at a fixed point within fluid path 101 and/or is otherwise relatively stably positioned in fluid path 101. In another embodiment, the surface (e.g., beads) may be combined with the fluid before it is flowed into fluid path 101. The surface may be captured as the fluid flows through fluid path 101 in order to concentrate the target substance.

As an example, where the target substance in the fluid is an analyte, beads having antibodies with specificity for the analyte may be combined with the fluid where the antibodies will capture the analyte. The fluid containing the beads with bound analyte thereon, may be flowed through fluid path 101 where the beads are captured, and fluid containing some or all of the beads is flowed onto the discrete flow section of droplet actuator 100 and formed into a droplet. The capture may for example, be accomplished using a magnetic field for magnetically responsive beads and/or physical barriers which may prevent beads from continuing to flow through fluid path 101. Once formed, bead-containing droplet may then be subjected to further droplet operations as part of a protocol for analyzing the analyte.

In one embodiment, opening 119 may be configured so that in the ordinary course of flowing fluid through fluid path 101, fluid does not enter the discrete flow section of droplet actuator 100 without some further assistance. For example, opening 119 may be configured so that it's width is smaller than the height of fluid path 101. In this manner, fluid may flow through fluid path 101 without readily passing through opening 119. Fluid can be prompted to flow through opening 119 by, for example, activating electrode 105 and/or restricting outflow from fluid path 101 while continuing to provide pressure from pressure source 115.

Fluid may be flowed through fluid path 101 using a variety of positive and/or negative pressure sources. For example, pressure source 115 may be gravity, capillarity or a syringe pushing or pulling fluid through fluid path 101. Various valves, such as valve 117, may be provided to control fluid flow through fluid path 101. For example, fluid outflow may be controlled by a valve 117 at outlet 111. A valve may be arranged to control application of a positive and/or negative pressure source for flowing fluid through fluid path 101. One or more valves may also be used to control the rate of fluid flow through fluid path 101.

The digital portion 113 of droplet actuator 100 may include electrode configurations for conducting any of a variety of droplet operations.

Barriers 103 and 107 may, for example, be formed from gasket material. Inferior portions of droplet actuator 100 may, in some embodiment, be made from or coated with a hydrophobic material. In another embodiment, surfaces of fluid path 101 may be made from and/or coated with a hydrophilic material. In one embodiment, the discrete flow section of droplet actuator 100 is covered or filled with a filler fluid that is immiscible with fluid in fluid path 101. Similarly, the filler fluid may be selected to be immiscible with droplets that are to be subjected to droplet operations mediated by electrode array 113, which may be any arrangement of electrodes suitable for conducting one or more droplet operations. A filler fluid/sample fluid interface (e.g., an oil/water interface) may be present at opening 119.

In the example illustrated in FIG. 1, fluid flows from inlet 109, through the fluid path 101, and out through outlet 111. Fluid not transported into the discrete flow section may be recirculated through the fluid path 101. Various other embodiments are contemplated in which the fluid flow is different. For example, there may be multiple openings 119 in barrier 103 which lead to fluid path 101. Similarly, there may be multiple openings in barrier 107 for introducing and/or removing fluid from fluid path 101. Further, fluid may be introduced and/or removed from fluid path 101 through barrier 103, barrier 107, the base substrate of droplet actuator 100 and/or the optional top plate of droplet actuator 100. Similarly, fluid path 101 may be a capillary or tube which passes through the discrete flow section of droplet actuator 100 and having openings therein for flowing fluid from inside the capillary or tube into proximity with one or more electrodes of droplet actuator 100.

Fluid path 101 is illustrated as being adjacent to electrodes 119 substantially on a common plane; however, it will be appreciated that fluid path 101 may be oriented in any direction relative to electrodes 119, e.g., above, alongside, and/or below electrodes 119. Further, multiple fluid paths 101 may be used for each electrode 119 and/or one or more of the electrodes 119 may be associated with a different fluid path 101.

Figure 2:
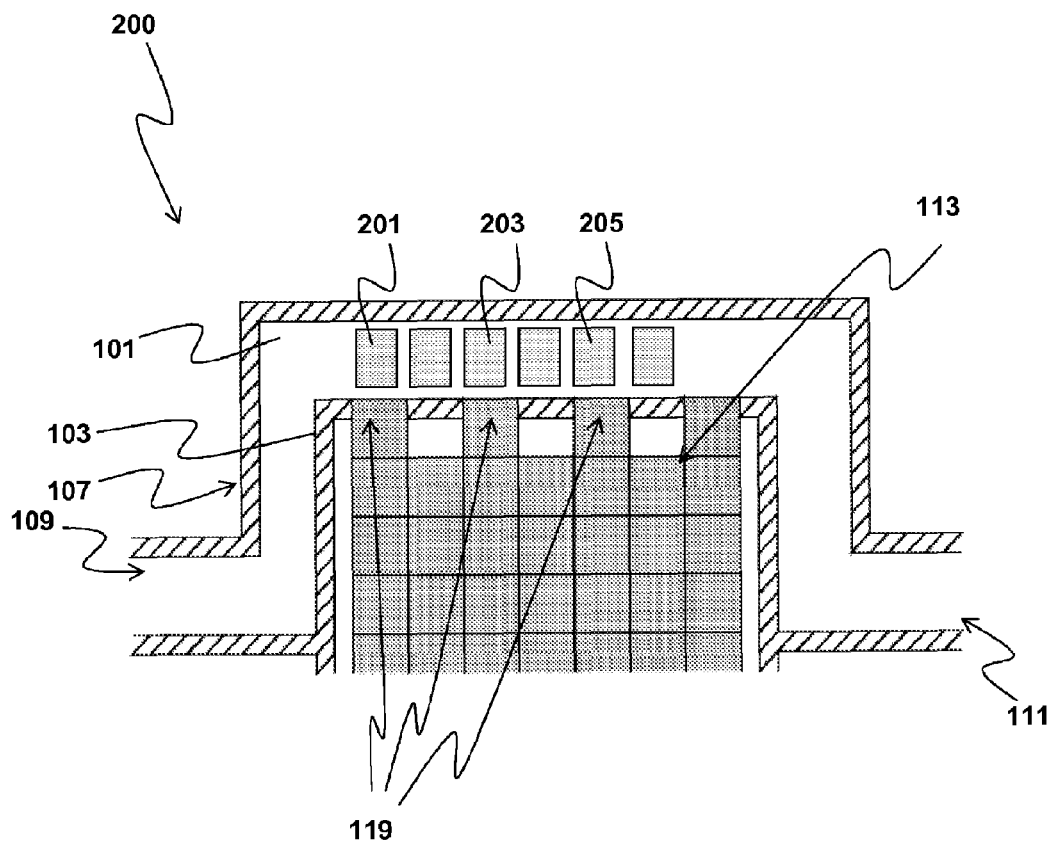
FIG. 2 illustrates a droplet actuator, which is like the droplet actuator of FIG. 1, except that it includes multiple target substance collection surfaces in fluid path and multiple openings.

FIG. 2 illustrates a droplet actuator 200, which is like droplet actuator 100 of FIG. 1, except that droplet actuator 200 includes multiple target substance collection surfaces 201, 203, 205 in fluid path 101, and further, droplet actuator 200 includes multiple openings 119.

In operation, a fluid containing a target substance may be floated into inlet 109, through fluid path 101, and out through outlet 111. Target substances in the input fluid may be captured at capture points 201, 203, and 205, etc. As described above, the target substance may be captured using a binder which is specific to the target substance. The surfaces may include beads (not shown).

In one embodiment, fluid path 101 also includes droplet operation electrodes arranged such that a droplet can be transported from the discrete flow section into fluid path 101. In this embodiment, a target substance may be captured on a surface of fluid path 101, e.g., at a capture point 201, 203, 205. A droplet comprising a fluid for releasing the target substance may be transported using electrode-mediated droplet operations from the discrete flow section onto the electrodes in fluid path 101 into contact with a capture point 201, 203, 205, where the droplet may release and absorb the target substance. The droplet, now including the target substance, may be transported back to the discrete flow section for further steps, e.g., in an assay to analyze the target substance.

In another related embodiment, following capture on capture point 201, 203, 205, a droplet containing assay reagents may be transported using electrode-mediated droplet operations from the discrete flow section onto the electrodes in fluid path 101 into contact with a capture point 201, 203, 205, where the reaction may occur and the product be detected using a detector in proximity with the droplet actuator. In alternative embodiment, the detection zone may be located in the discrete flow section, and a droplet from the assay region may be transported into the discrete flow section for detection.

In another related embodiment, following capture on capture point 201, 203, 205, a fluid for releasing the target substance may be flowed into contact with the capture point to release the captured target substance into the fluid. The fluid may be then flowed into the discrete flow section of the droplet actuator, where it may be formed into one or more droplets for conducting droplet operations.

Different capture sites may use the same or different capture means. For example, capture site 201 may utilize an antibody which binds to an antigen in the input fluid; capture site 203 may utilize an antigen which binds to an antibody in the input fluid; capture site 205 may utilize a nucleic acid which binds to nucleic acids in the input fluid. Accordingly, the different target substances are concentrated and separated.

Further, the fluid flowed into contact with the capture points 201, 203, 205 may be droplets contained in a filler fluid which is flowed through fluid path 101.

Figure 3:
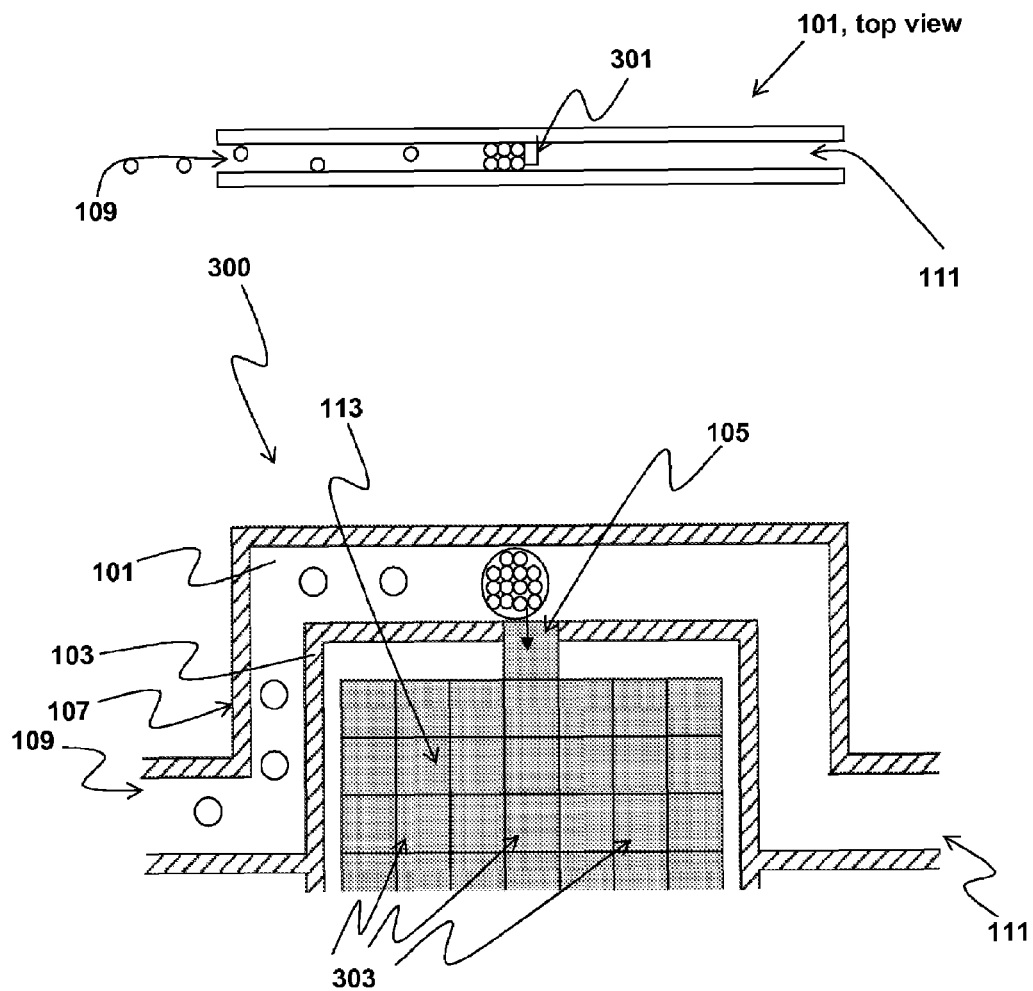
FIG. 3 illustrates a droplet actuator, which is like the droplet actuator of FIG. 1, except that it illustrates the use of a physical barrier to capture beads.

FIG. 3 illustrates a droplet actuator 300, which is like droplet actuator 100 of FIG. 1, except that droplet actuator 300 illustrates the use of a physical barrier to capture beads. In this embodiment, beads having affinity for a target substance may be combined with a fluid having the target substance. The target substance will bind to the beads. The beads may be concentrated, e.g., using a filter. In any case, a fluid comprising the beads is flowed through fluid path 101 where the beads are captured by barrier 301, while the fluid continues to flow through channel 101 and, in the embodiment illustrated, out outlet 111. Once sufficient beads have been captured, electrode 105 may be activated to pull a droplet into the discrete flow section of droplet actuator 300. Other means for forcing fluid into the discrete flow section of the droplet actuator, as described elsewhere, may also be used.

In some embodiment, the beads may include a mixture of bead populations, each bead population having one or more beads having specificity for a specific target substance. U.S. Patent Application No. 60/896,393, filed on Mar. 22, 2007, entitled "Sample preparation by beads sorting" and Related U.S. patent application Ser. No. 60/980,584, filed contemporaneously with this patent application, also entitled "Sample preparation by bead sorting," the entire disclosures of which are incorporated herein by reference, described droplet based approaches to sorting beads. Further, beads may be sorted on the droplet actuator using any approach which permits a difference in beads to be sensed in a droplet on a droplet actuator. Examples include different colored beads, beads with different levels of radioactivity, beads that absorb light differently, and many other approaches.

Figure 4:
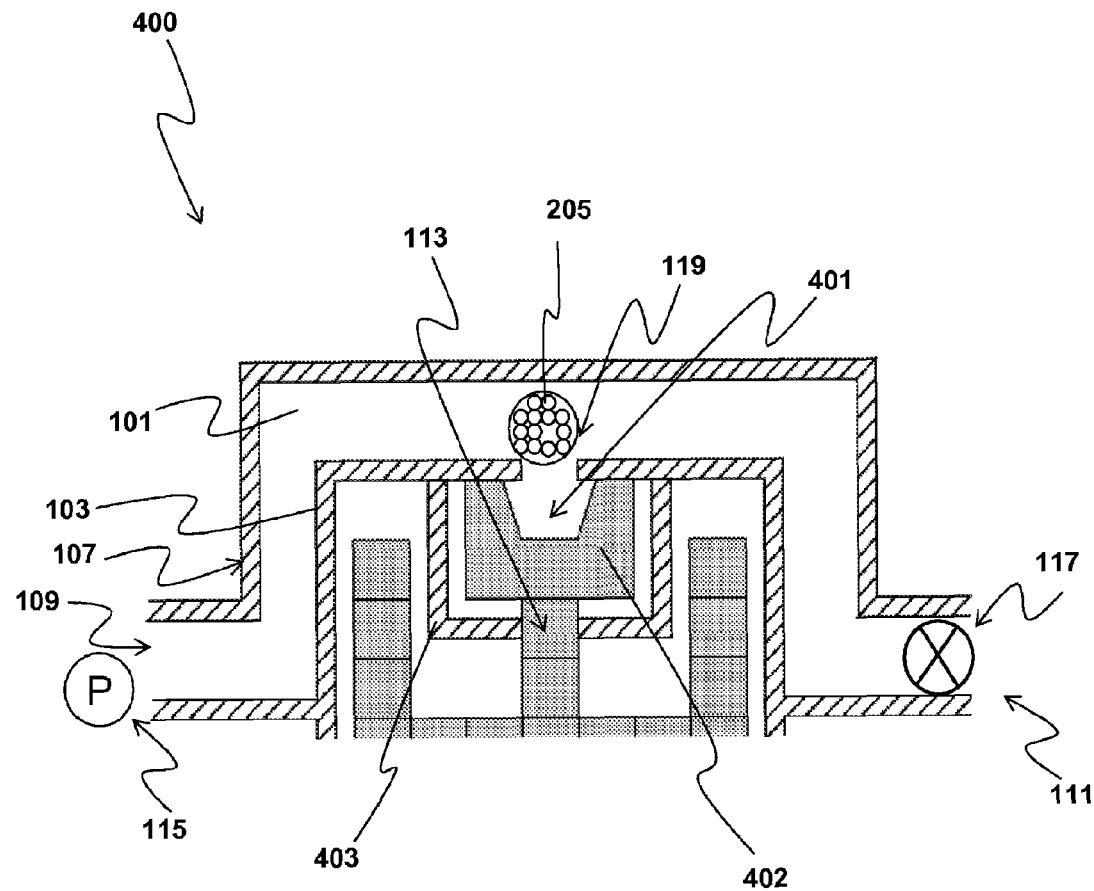
FIG. 4 illustrates a droplet actuator, which is like the droplet actuator of FIG. 3, except that FIG. 4 includes an illustration of the use of a dispensing reservoir.

FIG. 4 illustrates a droplet actuator 400, which is like droplet actuator 300 of FIG. 3, except that droplet actuator 400 illustrates the use of a dispensing reservoir 401. Dispensing reservoir 401 is located on the discrete flow section of droplet actuator 400. Opening 119 provides a fluid path from fluid path 101 into reservoir 401 and into proximity with reservoir electrode 402. Reservoir electrode 402 may optimally be bounded in part by a barrier 403. In operation, once sufficient beads are captured at capture point 205, fluid containing the beads may be flowed into reservoir 401, into contact with reservoir electrode 402. Fluid containing beads may then be dispensed from reservoir 401 as discrete, unit-sized droplets for further droplet operations.

Figure 5:
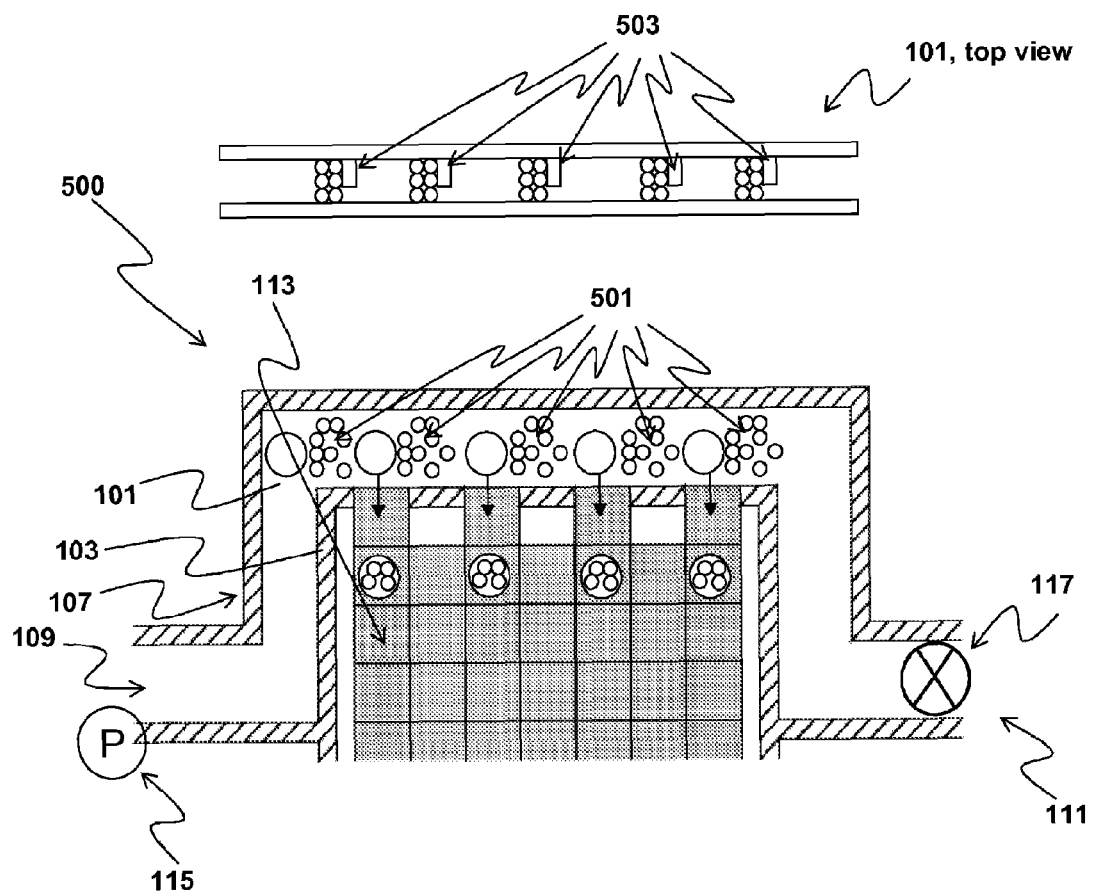
FIG. 5 illustrates a droplet actuator, which is like the droplet actuator of FIG. 3, except that FIG. 5 illustrates the use of a series of bead populations, each trapped in place by physical barriers.

FIG. 5 illustrates droplet actuator 500, which is like droplet actuator 300 of FIG. 3, except that droplet actuator 500 illustrates the use of a series of bead populations, each trapped in place by physical barriers. In operation, fluid flowed through fluid path 101 sequentially comes into contact with each of the bead populations. The populations may contain the same or different target substance binders. Once sufficient fluid has been contacted with each of the bead populations, droplets comprising the beads can be formed and manipulated using various droplet operations on the discrete flow section of droplet actuator 500.

In a related embodiment, droplet manipulation electrodes are provided in fluid path 101, and the electrodes are used to manipulate discrete droplets into contact with each of the bead populations, and into the discrete flow section of droplet actuator 500. In another related embodiment, filler fluid comprising droplets therein is flowed through fluid path 101, and each droplet is transported into the discrete flow section of the droplet actuator once it has contacted its bead population. Thus, for example, the first droplet may contact the first set of beads, and be transported into the discrete flow section of the droplet actuator. The second droplet may contact the second set of beads, and be transported into the droplet actuator, and so on. This approach has the advantage that each droplet contacts only one set of beads, preventing interference that may be caused by nonspecific binding.

Figure 6:
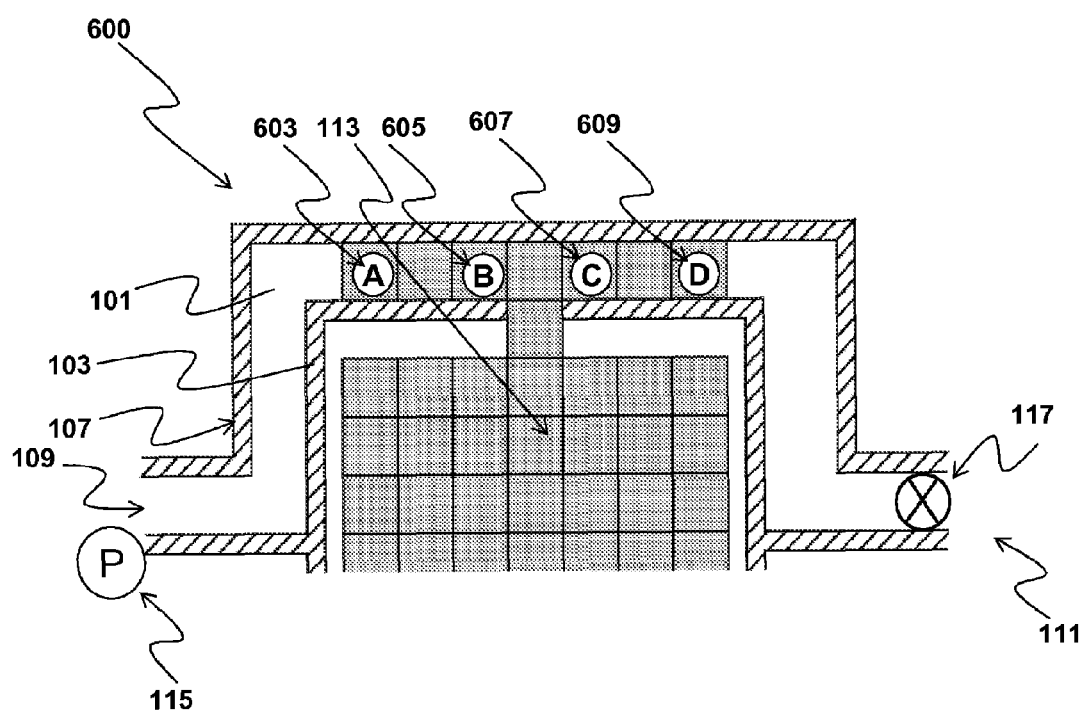
FIG. 6 illustrates a droplet actuator, which is like the droplet actuator of FIG. 1, except that FIG. 6 illustrates an embodiment in which fluid path includes electrodes arranged for conducting droplet operations.

FIG. 6 illustrates droplet actuator 600, which is like droplet actuator 100 of FIG. 1, except that droplet actuator 600 illustrates an embodiment in which fluid path 101 includes electrodes arranged for conducting droplet operations. One or more of the electrodes may be associated with a target substance capture site, e.g., capture sites A, B, C, D, associated with electrodes 603, 605, 607, 609. Fluid flowing through fluid path 101 interacts with the sites, permitting target substance to be captured. As described in other examples, capture may be accomplished by binding factors on the beads or other surfaces associated with the capture sites.

In one embodiment, fluid is flowed through fluid path 101 permitting target substance to be captured at capture sites A, B, C, D. Once capture sites A, B, C, D have been sufficiently exposed to input fluid, electrodes 603, 605, 607, 609, A, B, C, D are activated, and the remaining fluid is flushed from fluid path 101, e.g., by flowing oil through the fluid path. As a result, droplets remain on the activated electrodes 603, 605, 607, 609. These droplets may then be subjected to droplet operations using the electrodes in fluid path 101 and/or transported into the discrete flow section of the droplet actuator for further processing/analysis.

The capture sites 603, 605, 607, and 609 may be a labeled set of beads, or any other labeled surface attachment. An electrode is activated at the capture sites. As the oil flows through fluid path 101, the pressure is set to oust any sample liquid that is not at the capture sites. The liquid at the capture sites remains due to the activated electrode. Oil flows around the liquid at the capture sites, creating droplets in fluid path 101. In one embodiment, the capture sites include beads, and droplets including the beads are subjected to further droplet operations.

Figure 7:
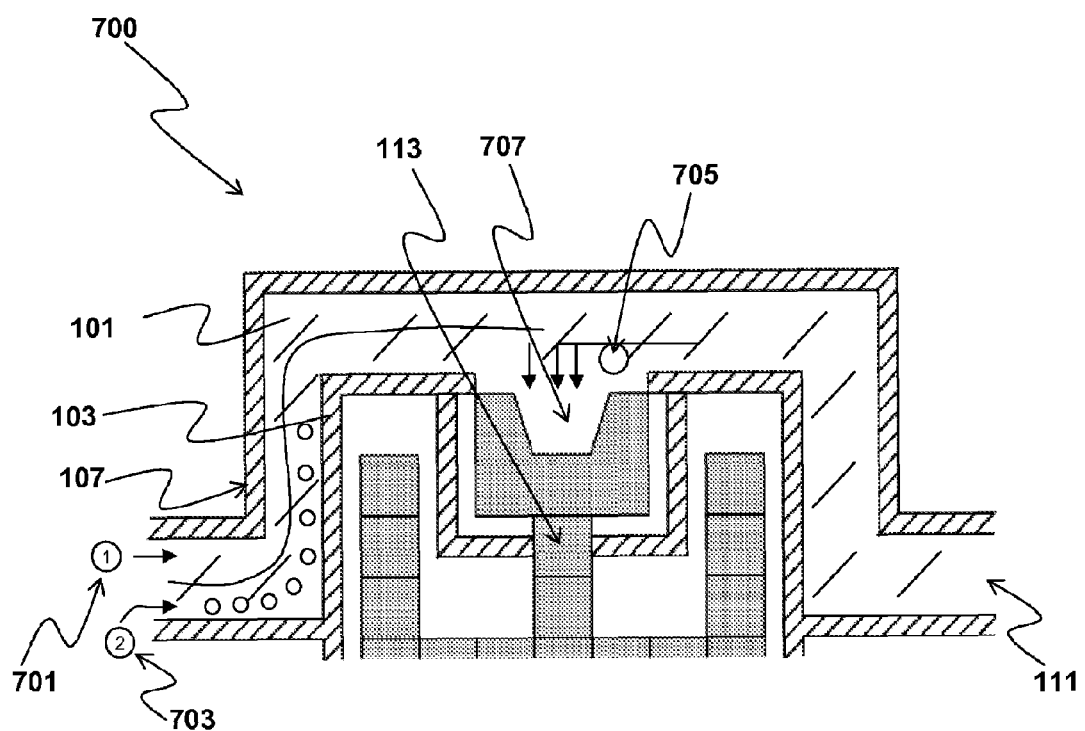
FIG. 7 illustrates a droplet actuator, which is like droplet actuator of FIG. 4, except that FIG. 7 illustrates an embodiment in which laminar flow of two liquids is employed to separate/concentrate target substance.

FIG. 7 illustrates droplet actuator 700, which is like droplet actuator 400 of FIG. 4, except that droplet actuator 700 illustrates an embodiment in which laminar flow of two liquids is employed to separate/concentrate target substance. The fluids may be flowed together through fluid path 101 of droplet actuator 700, with one fluid being flowed along an inner portion of fluid path 101, which is generally proximate relative to the discrete flow section of droplet actuator 700, and the other fluid being flowed along an outer portion of fluid path 101, which is generally distal relative to the discrete flowed section of droplet actuator 700. In one embodiment, one fluid is an aqueous solution, and the second fluid is a non-aqueous, such as acetone. Target substance may be extracted from the aqueous solution into the nonaqueous solution or vice versa. By controlling the flow of the solutions, fluid containing target substance may accumulate in reservoir 707. The flow of the solutions may be controlled by an H-filter. Droplets may then be dispensed from the reservoir into the discrete flow section of droplet actuator 700 for further processing/analysis.

This embodiment makes use of laminar flow of the liquids, which can result in a gradient in the concentration of materials. The concentration of the material may be a function of its position in fluid path 101. For example, one type of material concentrated on one side of the reservoir and one type of material may be concentrated on the other side of the reservoir. Sampling may be controlled effectively obtain droplets enriched for one type of material or another.

In an embodiment, the input fluid may be blood, and the second solution may be buffer. As the solutions flow through fluid path 101, blood components may adhere to surfaces along fluid path 101. Smaller molecules from the blood may diffuse into the buffer, and larger cells such as white blood cells may remain in the blood. Similarly, the flow may be controlled to permit transfer of the white blood cells to the reservoir.

In any of the various embodiments described herein, fluid may in some cases be recirculated through fluid path 101, e.g., to improve capture of analytes.

Further, the fluid flowed through fluid path 101 may be a filler fluid containing droplets. Some or all of the droplets may be diverted into the discrete flow section of the droplet actuator for processing using the various approaches described herein.

7.2 Droplet Actuator

For examples of droplet actuator architectures suitable for use with the present invention, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. Nos. 6,773,566, entitled "Electrostatic Actuators for Microfluidics and Methods for Using Same," issued on Aug. 10, 2004 and 6,565,727, entitled "Actuators for Microfluidics Without Moving Parts," issued on Jan. 24, 2000, both to Shenderov et al.; Pollack et al., International Patent Application No. PCT/US 06/47486, entitled "Droplet-Based Biochemistry," filed on Dec. 11, 2006, the disclosures of which are incorporated herein by reference. Examples of droplet actuator techniques for immobilizing magnetic beads and/or non-magnetic beads are described in the foregoing international patent applications and in Sista, et al., U.S. Patent Application Nos. 60/900,653, filed on Feb. 9, 2007, entitled "Immobilization of magnetically-responsive beads during droplet operations"; Sista et al., U.S. Patent Application No. 60/969,736, filed on Sep. 4, 2007, entitled "Droplet Actuator Assay Improvements"; and Allen et al., U.S. Patent Application No. 60/957,717, filed on Aug. 24, 2007, entitled "Bead washing using physical barriers," the entire disclosures of which is incorporated herein by reference.

7.3 Fluids

For examples of fluids usefully processed according to the approach of the invention, see the patents listed in section 6.2, especially International Patent Application No. PCT/US 06/47486, entitled "Droplet-Based Biochemistry," filed on Dec. 11, 2006. In some embodiments, the input fluid includes or consists of a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes.

7.4 Filler Fluids

The gap will typically be filled with a filler fluid. The filler fluid may, for example, be a low-viscosity oil, such as silicone oil. Other examples of filler fluids are provided in International Patent Application No. PCT/US 06/47486, entitled "Droplet-Based Biochemistry," filed on Dec. 11, 2006.

This specification is divided into sections for the convenience of the reader only. Headings should not be construed as limiting of the scope of the invention.

It will be understood that various details of the present invention may be changed without departing from the scope of the present invention. Various aspects of each embodiment described here may be interchanged with various aspects of other embodiments. Furthermore, the foregoing description is for the purpose of illustration only, and not for the purpose of limitation.

We claim:

1. A method of providing a droplet comprising an target substance on a droplet actuator, the method comprising:
   (a) providing a droplet actuator comprising a substrate comprising:

(i) a discrete flow section comprising electrodes arranged for conducting droplet operations on a substrate surface;

(ii) a continuous flow section comprising a fluid path arranged for flowing a fluid therethrough, and separated from the discrete flow section by a barrier;

(iii) an opening in the barrier arranged relative to the electrodes such that fluid in the fluid path is in proximity to one or more of the electrodes;

(iv) a capture surface comprising a component having an affinity for the target substance;

(b) flowing a fluid comprising the target substance through the fluid path;

(c) capturing the target substance on the capture surface; and (d) forming a droplet comprising the captured target substance in the discrete flow section.

2. The method of claim 1 further comprising transporting the target substance through the opening and into the discrete flow section.

3. The method of claim 1 wherein step 1(d) comprises conducting droplet operations using the electrodes to draw fluid comprising the sample of interest through the opening and forming a droplet therefrom.

4. The method of claim 1 wherein the droplet actuator further comprises sample collection beads immobilized in the fluid path such that a target substance in a fluid flowing through the fluid path is collected on the beads, and step 1(d) comprises transporting a droplet comprising the beads through the opening and into the droplet actuation region.

5. The method of claim 1 wherein the droplet formed in step 1(d) is at least partially surrounded by a filler fluid.

6. The method of claim 1 wherein the droplet formed in step 1(d) is substantially completely surrounded by a filler fluid.

7. The method of claim 1 wherein the droplet formed in step 1(d) comprises one or more beads.

8. The method of claim 1 wherein the droplet formed in step 1(d) comprises one or more biological cells.

9. The method of claim 1 wherein the width of the opening is smaller than the height of the fluid path.

10. The method of claim 1 wherein the continuous flow section comprises a second set of electrodes arranged for conducting droplet operations, and the method further comprises:
(a) forming one or more sample droplets on the second set of electrodes; and
(b) transporting said one or more sample droplets into the discrete flow section.

11. The method of claim 1 wherein the continuous flow section comprises a second set of electrodes arranged for conducting droplet operations, and the method further comprises:
(a) forming one or more sample droplets on the second set of electrodes; and
(b) using the second set of electrodes to transport said one or more sample droplets into proximity with electrodes in the discrete flow section.

12. The method of claim 1 comprising two or more capture surfaces in the continuous flow section.

13. The method of claim 12 wherein the two or more capture surfaces each comprise a population of beads, wherein each population has affinity for a different target substance.

14. The method of claim 13 wherein the beads are maintained in place by one or more physical barriers.

15. The method of claim 13 wherein the beads are magnetically responsive and are maintained in place by one or more magnetic fields.

16. The method of claim 15 wherein the magnetic field comprises a magnetic field produced by an electromagnet.

17. The method of claim 15 wherein the magnetic field comprises a magnetic field produced by a permanent magnet.

18. The method of claim 1 wherein step 1(c) comprises combining one or more beads having affinity for the target substance with a fluid comprising the target substance prior to introduction of the fluid into the fluid path.

19. The method of claim 1 wherein the target substance comprises an analyte of interest.

20. The method of claim 1 wherein the target substance comprises a product of a chemical reaction.

21. The method of claim 1 wherein the target substance comprises a bead.

22. The method of claim 1 wherein the target substance comprises a biological cell.

23. The method of claim 1 wherein the target substance comprises a bead comprising an analyte of interest and/or a product of a chemical reaction.

24. The method of claim 1 wherein the discrete flow section is separated from the continuous flow section by a reservoir comprising a reservoir electrode.

25. The method of claim 24 wherein the method comprises:
(a) flowing a fluid comprising the substance of interest from the fluid path into the reservoir; and
(b) dispensing droplets from the reservoir onto one or more electrodes in the discrete flow section.

26. The method of claim 1 wherein step 1(b) comprises forcing fluid through the fluid path using a pressure source.

27. The method of claim 26 wherein the pressure source comprises a syringe coupled to the fluid path.

28. The method of claim 1 wherein step 1(d) comprises activating one of more electrodes in the discrete flow section adjacent to the opening to cause fluid to flow from the fluid path into the discrete flow section and form the droplet.

29. The method of claim 1 wherein step 1(d) comprises forcing fluid from the fluid path through the opening into the discrete flow section into proximity with one or more electrodes, and conducting droplet operations using the one of more electrodes to form the droplet.

30. The method of claim 29 wherein the forcing fluid step comprises causing a pressure in the fluid path which forces fluid through the opening into the discrete flow section into proximity with the one or more electrodes.

31. A droplet actuator comprising a substrate comprising:
(a) a discrete flow section comprising electrodes arranged for conducting droplet operations on a substrate surface;
(b) a continuous flow section comprising a fluid path arranged for flowing a fluid therethrough, and separated from the discrete flow section by a barrier;
(c) sample collection beads immobilized in the fluid path;
(d) an opening in the barrier arranged relative to the electrodes such that fluid in the fluid path is in proximity to one or more of the electrodes; and
(e) a capture surface comprising a component having an affinity for the target substance.

32. A droplet actuator comprising a substrate comprising:
(a) a discrete flow section comprising electrodes arranged for conducting droplet operations on a substrate surface;
(b) a continuous flow section comprising a fluid path arranged for flowing a fluid therethrough, and separated from the discrete flow section by a barrier;
(c) two or more capture surfaces in the continuous flow section;

(d) an opening in the barrier arranged relative to the electrodes such that fluid in the fluid path is in proximity to one or more of the electrodes; and (e) a capture surface comprising a component having an affinity for the target substance.

33. The method of claim 32 wherein the two or more capture surfaces each comprise a population of beads, wherein each population has affinity for a different target substance.

34. The method of claim 33 wherein the beads are maintained in place by one or more physical barriers.

35. The method of claim 33 wherein the beads are magnetically responsive and are maintained in place by one or more magnetic fields.

36. The method of claim 35 wherein the magnetic field comprises a magnetic field committed by an electromagnet.

37. The method of claim 35 wherein the magnetic field comprises a magnetic field committed by a permanent magnet.

* * * * *